United States Patent [19]

Hermann et al.

[11] Patent Number: 5,606,036
[45] Date of Patent: Feb. 25, 1997

[54] ANTIBIOTIC A 40926 ESTER DERIVATIVES

[75] Inventors: Rolf H. Hermann, Milan; Romeo Ciabatti, Novate Milanese; Enrico Selva, Gropello Cairoli; Maurizio Denaro, Opera, all of Italy

[73] Assignee: Gruppo Lepetit SpA, Gerenzano, Italy

[21] Appl. No.: 447,152

[22] Filed: May 22, 1995

Related U.S. Application Data

[63] Continuation of Ser. No. 305,615, Sep. 14, 1994, abandoned, which is a continuation of Ser. No. 117,048, Sep. 9, 1993, abandoned.

[30] Foreign Application Priority Data

Mar. 27, 1991 [EP] European Pat. Off. ............ 91104857

[51] Int. Cl.$^6$ .............................. C07H 15/20; C07H 17/08
[52] U.S. Cl. ........................... 536/4.1; 536/7.1; 536/17.2; 536/17.3; 536/17.4; 536/115; 536/120
[58] Field of Search ..................... 424/118, 119, 424/120; 514/27, 183; 536/16.8, 17.2, 17.3, 17.4, 17.9, 18.1, 18.5, 4.1

[56] References Cited

U.S. PATENT DOCUMENTS

| | | | |
|---|---|---|---|
| 4,239,751 | 12/1980 | Coronelli et al. | 424/118 |
| 4,542,018 | 9/1985 | Borghi et al. | 424/119 |
| 4,661,470 | 4/1987 | Malabarba et al. | 514/9 |
| 4,782,042 | 11/1988 | Selva et al. | 514/9 |
| 4,868,171 | 9/1989 | Selva et al. | 514/183 |
| 4,914,187 | 4/1990 | Malabarba et al. | 530/317 |
| 4,935,238 | 6/1990 | Selva et al. | 424/118 |
| 4,954,483 | 9/1990 | Malabarba et al. | 514/9 |
| 5,064,811 | 11/1991 | Borghi et al. | 514/8 |

FOREIGN PATENT DOCUMENTS

| | | |
|---|---|---|
| 0228015 | 12/1986 | European Pat. Off. |
| 0259781 | 3/1987 | European Pat. Off. |
| 0376041 | 12/1989 | European Pat. Off. |
| 0525499 | 7/1992 | European Pat. Off. |
| 8802755 | 4/1988 | WIPO |

OTHER PUBLICATIONS

Synthesis & Biological Activity of Some Esters of the N–Acetylglucosaminyl Aglycone and of the Aglycone of Teicoplanin; The Journal of Antibiotics; A. Malabarba, et al., vol. 40(11): 1572–1587, (1987).

Malabarba, et al; Semi–synthetic teicoplanin antibiotics; Current Patents, vol. 2, pp. 263–287 (1990).

*Primary Examiner*—Gary L. Kunz
*Assistant Examiner*—Howard C. Lee
*Attorney, Agent, or Firm*—J. Michael Dixon

[57] ABSTRACT

The present invention relates to novel ester derivatives of antibiotic A 40926 complex and its N-acylaminoglucuronyl aglycone. The compounds of the invention are prepared according to an esterification process involving reaction of an A 40926 substrate with an excess of the selected alkanol in the presence of concentrated mineral acid and are reactive as antibiotics.

8 Claims, No Drawings

ANTIBIOTIC A 40926 ESTER DERIVATIVES

This is a continuation of application Ser. No. 08/305,615, filed Sep. 14, 1994, now abandoned, which is a continuation of application Ser. No. 08/117,048, filed Sep. 9, 1993, now abandoned herein incorporated by reference.

The present invention is directed to new antibiotic A 40926 ester derivatives of formula I

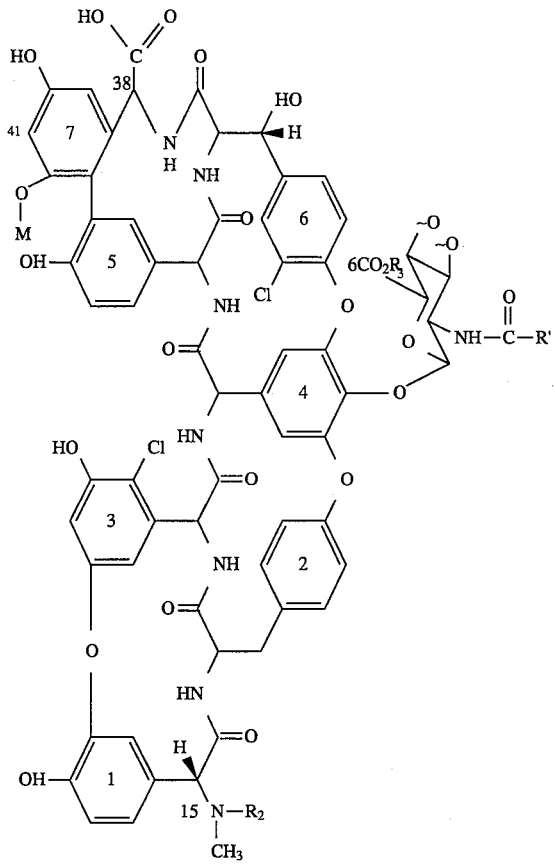

wherein $R_2$ represents hydrogen or a protecting group of the amine function;

M represents hydrogen, α-D-mannopyranosyl or 6-O-acetyl-α-D-mannopyranosyl;

R' represents $(C_{10}-C_{11})$ alkyl;

$R_3$ represents $(C_1-C_6)$ alkyl, hydroxy$(C_1-C_6)$ alkyl or halo$(C_1-C_6)$alkyl;

and the addition salts thereof.

As used herein the term "alkyl", either alone or in combination with other substituents, includes both straight and branched hydrocarbon groups; more particularly, "$(C_1-C_6)$alkyl" represents a straight or branched aliphatic hydrocarbon chain of 1 to 6 carbon atoms such as methyl, ethyl, propyl, 1-methylethyl, butyl, 1-methylpropyl, 1,1-dimethylethyl, pentyl, 1-methylbutyl, 2-methylbutyl, hexyl, 1-methylpentyl, 3,3-dimethylbutyl, 1-ethylbutyl, 4-methylpentyl, 3-methylpentyl, and the like.

The term "halo$(C_1-C_6)$alkyl" represents mono- or poly-halogenated alkyl groups of 1 to 6 carbon atoms wherein the halo atoms can be chloro, fluoro, or bromo and can be situated on any carbon atom of the alkyl chain.

Preferably the "halo$(C_1-C_6)$alkyl" groups contain a number of halo atoms ranging between 1 and 3, most preferably being monosubstituted.

Examples of "halo$(C_1-C_6)$alkyl" groups are: 2-chloroethyl, 1-chloroethyl, 2-bromoethyl, 2,2-dichloroethyl, 2,2-dibromoethyl, 2-fluoroethyl, 3-chloropropyl, 3-bromopropyl, 3,3,3-tribromopropyl, 3-fluoropropyl, 2-chloropropyl, 2-bromopropyl, 2-fluoropropyl, 4-chlorobutyl, 4-bromobutyl, 4-fluorobutyl, 3-bromobutyl, 3-chlorobutyl and the like.

The term "hydroxy$(C_1-C_6)$alkyl" represents mono- or poly-hydroxy alkyl groups of 1 to 6 carbon atoms wherein the hydroxy groups can be on any carbon atom of the alkyl chain, with the proviso that each carbon can not contain more than one hydroxy group.

Preferably the "hydroxy$(C_1-C_6)$alkyl group contain a number of hydroxy atoms ranging between 1 and 3, most preferably being monosubstituted.

Examples of "hydroxy$(C_1-C_6)$alkyl" groups are: 2-hydroxyethyl, 3-hydroxypropyl, 2-hydroxypropyl, 2,3-dihydroxypropyl, 4-hydroxybutyl, 2-hydroxybutyl, 3-hydroxybutyl, and the like.

The N-protecting group which may be used in the present invention is one of the N-protecting groups known in the art such as those described in reference books (see for instance T. W. Greene, "Protective Groups in Organic Chemistry", John Wiley and Sons, New York, 1981, p. 323–326, and M. Mc. Omie "Protecting Groups in Organic Chemistry", Plenum Press, New York, 1973) which is capable of forming a bond with the primary amino group in position 15 of the antibiotics of formula I.

A preferred N-protecting group is benzyl.

Antibiotic A 40926 is a glycopeptide antibiotic which has been isolated from a culture of Actinomadura, named Actinomadura sp. ATCC 39727, in a culture medium containing assimilable sources of carbon, nitrogen, and inorganic salts (see EP-A-177882). According to the procedure described in the above cited patent the recovery of the antibiotic complex, whose factors have been named factor A, factor B, factor $B_0$, factor PA, and factor PB, includes submitting the fermentation broths, after filtration or after a preliminary purification procedure, to affinity chromatography on immobilized D-alanyl-D-alanine.

The A 40926 factors can be represented by the above formula I wherein $R_2$ and $R_3$ are hydrogen, R' represents a $(C_{10}-C_{11})$alkyl group, and M represents an α-D-mannopyranosyl or a 6-O-acetyl-α-D-mannopyranosyl group.

More particularly, antibiotic A 40926 factor A is a compound of the above formula I wherein R' represents n-decyl and M represents α-D-mannopyranosyl, antibiotic A 40926 factor $B_0$, the main component of factor B, is the compound of the above formula I wherein R' represents 9-methyldecyl and M represents α-D-mannopyranosyl.

Antibiotic A 40926 factor PA and factor PB differ from the corresponding factor A and B in that the mannose unit is replaced by a 6-O-acetyl-α-D-mannopyranose unit.

Antibiotic A 40926 factors PA and PB, at least under certain fermentation conditions, are the main antibiotic products of the A 40926 producing microorganism.

Antibiotic A 40926 factors A and B are mainly transformation products of antibiotics A 40926 factor PA and factor PB, respectively, and are often already present in the fermentation broths.

All the sugar moieties are linked to the antibiotic A 40926 nucleus through O-glycosidic bonds.

It has been found that antibiotic A 40926 factor PA can be transformed into antibiotic A 40926 factor A and antibiotic A 40926 factor PB can be transformed into antibiotic A 40926 factor B under basic conditions which lead to the removal of the acetyl group of the mannose unit without displacing the acyl group on the aminoglucuronyl unit.

As a consequence, when the fermentation broth, or an antibiotic A 40926 containing extract or concentrate thereof, is allowed to stand for a certain time under basic conditions (e.g. aqueous solution of a nucleophilic base, at a pH>9 overnight) an antibiotic A 40926 complex will be obtained which is enriched in antibiotics A 40926 factor A and factor B.

During the purification procedures of antibiotic A 40926 complex factors PA and PB are largely converted to factors A and B.

In addition it has been found that it is possible to transform antibiotic A 40926 complex, its single factors or mixture of said factors in any proportion into the corresponding N-acylaminoglucuronyl aglycone complex AB, N-acylaminoglucuronyl aglycone factor A, N-acylaminoglucuronyl aglycone factor B, and the mannosyl aglycone by controlled acid hydrolysis of one of the sugar moieties (see EP-A-240609 and EP-A-228015).

Preferred hydrolysis conditions for the production of N-acylaminoglucuronyl aglycones comprise the usage of a mixture of dimethylsulfoxide/concentrated hydrochloric acid from 8:2 to 9.5:0.5 at a temperature between 40° C. and 80° C.

Antibiotics A 40926 N-acylaminoglucuronyl aglycones are represented by the above formula I wherein $R_2$, $R_3$, and M are hydrogen, and R' is $(C_{10}-C_{11})$alkyl.

The complete cleavage of all the sugar moieties of the A 40926 antibiotics gives the aglycone. This hydrolysis process is described in EP-A-240609.

Antibiotic A 40926 complex, the factors thereof, the corresponding N-acylaminoglucuronyl aglycones, the deacyl derivatives, the mannosyl aglycone, the aglycone, and mixtures thereof in any proportion are mainly active against gram positive bacteria and Neisseriae.

Antibiotic A 40926 complex and its N-acylaminoglucuronyl aglycones are suitable starting materials for the preparation of the antibiotic A 40926 derivatives of formula I.

The compounds of this invention possess acid and basic functions and can form salts with organic and inorganic counter ions according to conventional procedures.

Representative and suitable acid addition salts of the compounds of the present invention include those salts formed by standard reaction with both organic and inorganic acids such as, for example, hydrochloric, hydrobromic, sulfuric, phosphoric, acetic, trifluorocetic, trichloroacetic, succinic, citric, ascorbic, lactic, maleic, fumaric, palmitic, cholic, pamoic, mucic, glutamic, campboric, glutaric, glycolic, phthalic, tartaric, laurie, stoatic, salicylic, methanesulfonic, benzenesulfonic, sorbic, picric, benzoic, cinnamic, and the like acids.

Representative examples of the bases that can form salts with the compounds of the present invention are: alkali metal or alkaline-earth-metal hydroxides such as sodium, potassium, calcium, magnesium, barium hydroxide; ammonia and aliphatic, allcyclic or aromatic organic amines such as methylamine, dimethylamine, trimethylamine, and picoline.

The transformation of the "non-salt" compounds of the invention into the corresponding addition salts, and the reverse, i.e. the transformation of an addition salt of a compound of the invention into the non-salt form, are within the ordinary technical skill and are encompassed by the present invention.

For instance, a compound of formula I can be transformed into the corresponding salts with acids or bases by dissolving the non-salt form in an aqueous solvent and adding a slight molar excess of the selected acid or base. The resulting solution or suspension is then lyophilized to recover the desired salt.

In case the final salt is insoluble in an organic solvent where the non-salt form is soluble, it is recovered by filtration from the organic solution of the non-salt form after adding the stoichiometric amount or a slight molar excess of the selected acid or base.

The non-salt form can be prepared from a corresponding salt dissolved in an aqueous solvent which is then neutralized to free the non-salt form. This is then recovered for instance by extraction with an organic solvent or is transformed into another addition salt by adding the selected acid or base and working up as above.

When following the neutralization, desalting is necessary, a common desalting procedure may be employed.

For example, column chromatography on controlled pore polydextrane resins (such as Sephadex L H 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water from 50:50 to about 100% acetonitrile.

As it is known in the art, the salt formation either with pharmaceutically acceptable acids and bases or non-pharmaceutically acceptable acids and bases may be used as a convenient purification technique. After formation and isolation, the salt form of a compound of formula I can be transformed into the corresponding non-salt or into a pharmaceutically acceptable salt.

However, in view of the similarity of the properties of the compounds of formula 1 and their salts, what is said in the present application when dealing with the biological activities of the compounds of formula I applies also to their pharmaceutically acceptable salts, and viceversa.

The compounds of this invention are useful as semi-synthetic antibacterial agents mainly active against gram-positive bacteria and Neisseriae.

Preferred compounds are those compounds of formula I wherein R' is $(C_{10}-C_{11})$alkyl, $R_2$ is hydrogen or benzyl, $R_3$ is $(C_1-C_4)$alkyl, hydroxy$(C_1-C_4)$alkyl, halo$(C_1-C_4)$ alkyl, M is hydrogen or α-D-mannopyranosyl.

A more preferred group of compounds is represented by those compounds of the formula I wherein R' is $(C_{10}-C_{11})$ alkyl, $R_2$ is hydrogen, $R_3$ is methyl or 2-hydroxyethyl, and M is α-D-mannopyanosyl.

General procedures can be applied to the esterification process of the compounds of formula I but, of course, in the esterification process of compounds of formula I two carboxy group are present, the carboxy group of the N-acylaminoglucuronyl moiety and the carboxy group in position 38 of the peptide core, whose reactivities are quite different.

General procedures for preparing ester derivatives of the present invention include reacting the $N_{15}$-protected or free-amino A 40926 substrate or its demannosyl derivative (i.e. N-acylaminoglucuronyl aglycone) with an alcohol in an acidic medium, or a $N_{15}$-protected A 40926 derivative or its demannosyl analogue with an alkyl halide (preferably bromide, chloride or iodide) optionally in the presence of an hydrohalic acid acceptor.

More particularly, controlled esterification procedures useful for preparing A 40926 ester derivatives and demannosyl A40926 ester derivatives include esterification reactions wherein the A 40926 substrate is brought together with an excess of the selected alkanol in the presence of concentrated mineral acid at a temperature between 0° C. and room temperature for a time varying with the steric complexity of the group that must be introduced (e.g. for the preparation of A 40926 $6^B$-alkyl esters, esterified at the carboxy group present on the N-acylamino glucuronyl moiety); and esterification reactions wherein the A 40926 substrate is brought-together with an excess of haloalkanol without any presence of acids (e.g. for the preparation of A 40926 $6^B$-haloalkyl esters).

In some instances it is convenient to protect the primary amino function in position 15 of the A 40926 starting material in order to reduce possible undesired side-reactions. This can be done by methods known per se in the art such as those described in reference books like T. W. Greene, "Protective Groups in Organic Synthesis" John Wiley and Sons, New York, 1981, and M. Mc Omie "Protecting Groups in Organic Chemistry" Plenum Press, New York, 1973. These protecting groups must be stable at the conditions of the reaction process, must not unfavorably interfere with the main reaction, and must be easily cleavable at the end of the main reaction.

The tert-butoxycarbonyl (tBOC), carbobenzyloxy (Cbz), and arylalkyl groups are example of suitable amino protecting groups. Probably due to steric hindrance the protection with carbamate forming reagents is more difficult than for other glycopeptide antibiotics of the ristocetin class having a free amino group at position 15. On the contrary the benzylation with optionally substituted benzyl halides in the presence of a base takes place smoothly with quantitative yield and leads exclusively to the formation of the corresponding $N_{15}$-benzyl derivative without the concomitant formation of an aralkyl ester of the carboxy groups.

Selective protection of the amino group at position 15 may be preferably carried out by reaction with benzyl bromide in the presence of an hydrogen halide acceptor (i.e. a tertiary amine) without concomitant esterification of the two carboxy groups.

The conditions of removal of the $N_{15}$-protecting groups are falling within those known in the art for the removal of the amino protecting groups and must be set up after an evaluation of the reactivity of other groups present in the molecules. Obviously, when the final compound of formula I contains groups which are labile under acidic conditions, e.g. when G and M represent sugar moieties as above defined which may be hydrolyzed in an acidic medium, other removal conditions must be used, such as catalytic hydrogenation, using for instance palladium on carbon as the catalyst to remove the proper protecting group. In this case, however, attention should be paid to the presence of groups which could be modified by catalytic hydrogenation.

In addition, the mannose moiety of a compound of formula I may be selectively removed to transform it into another compound of formula I wherein the mannose rest is replaced by hydrogen.

A compound of formula I wherein M is α-D-mannopyranosyl or 6-O-acetyl-α-D-mannopyranosyl, and $R_3$ is alkyl can be transformed into the corresponding compound wherein $R_3$ is as above, and M is hydrogen by means of selective acid hydrolysis. As disclosed in EP-A-240609 preferred hydrolysis conditions for the production of demannosyl A 40926 complex (i.e.: N-acylaminoglucuronyl aglycone) comprises the usage of a mixture of dimethylsulfoxide/concentrated hydrochloric acid from 8:2 (v/v) to 9.5:0.5 (v/v) at a temperature of 65° C.

Accordingly, the demannosyl derivatives of the esters of A 40926 can be obtained in a mixture with the corresponding aglycone that can be separated by preparative HPLC.

The hydrolytic conditions may be suitably modified to change the ratio between the resulting products. For instance, starting from A 40926 esterified in position $6^B$ of the N-acylaminoglucuronyl moiety, by using a solvent/hydrochloric acid ratio of 78:1, keeping the reaction temperature below 60° C. and increasing the reaction times to about 7 days, the ratio of the desired demannosyl A 40926, esterified at position $6^B$ of the N-acylaminoglucuronyl moiety, to the undesired aglycone of A 40926 results of about 1.4:1.0.

The reaction courses are monitored by HPLC according to methods known in the art.

On the basis of the results of these assays, a man skilled in the art will be able to evaluate the reaction course and decide when to stop the reaction and start working up the reaction mass according to known per se techniques which include, for instance, extraction with solvents, precipitation by non-solvents, in conjunction with further separation and purification by chromatography.

The antibacterial activity of the compounds of the present invention was determined in vitro by means of standard microbroth dilution methodology. Minimal inhibitory concentration (MIC) is considered as the lowest concentration which shows no visible growth after 18–24 h incubation at 37° C. MIC for *Clostridium difficile, Propionibacterium acnes,* and *Bacteroides fragilis* were determined by the agar dilution method. Unless otherwise indicated, inocula were approximately $10^4$ cfu (colony forming units)/ml or per spot. Incubation times were 18–24 hours, except for: *N. gonorrhoeae, Haemophilus influenzae, Clostridium difficile, Propionibacterium acnes,* and *Bacteroides fragilis* (48 hours). All the organisms were incubated at 37° C. *Neisseria gonorrhoeae* and *Haemophilus influenzae* were incubated in a 5% $CO_2$ atmophere; anaerobes were incubated in an anaerobic gas mixture. Media used were: Oxoid Iso-sensitest broth (staphylococci, *Enterococcus faecalis, Escherichia coli*); Difco Todd-Hewitt broth (streptococci); Difco GC base broth with 1% BBL IsoVitalex for *N. gonorrhoeae;* Difco Brain-Heart Infusion broth with 1% Difco supplement C for *H. influenzae;* Difco AC medium without agar for *Clostridium perfringens;* Oxoid Wilkins-Chalgren agar for the other anaerobes.

The results of the antibacterial testing of representative compounds of formula I are summarized in Table I below:

TABLE I

| | In vitro antibacterial activity of A 40926 derivatives | | | | | | | | | | | |
|---|---|---|---|---|---|---|---|---|---|---|---|---|
| | | | MIC (mcg/ml) | | | | | | | | | |
| Organism | A 40926 | A 40926 Aglycone | I | II | III | IV | V | VI | VII | VIII | IX | X |
| *Staphylococcus aureus* L165 | 0.13 | 0.13 | 0.13 | 0.13 | 0.5 | 0.25 | 0.13 | 0.25 | 0.13 | 0.13 | 0.25 | 0.06 |
| *S. epidermidis* ATCC 12228 | 0.13 | 0.13 | 0.25 | 0.25 | 2 | 0.13 | 1 | 2 | 0.25 | 0.13 | 0.25 | 0.06 |
| *S. haemolyticus* L602 | 4 | 0.5 | 4 | 8 | 16 | 16 | 8 | 16 | 4 | 0.5 | 4 | 0.5 |

TABLE I-continued

In vitro antibacterial activity of A 40926 derivatives

| Organism | A 40926 | A 40926 Aglycone | I | II | III | IV | V | VI | VII | VIII | IX | X |
|---|---|---|---|---|---|---|---|---|---|---|---|---|
| *Streptococcus pyogenes* C203 | 0.03 | 0.5 | 0.06 | 0.06 | 0.06 | 0.06 | 0.06 | 0.06 | 0.06 | 0.06 | 0.06 | 0.06 |
| *S. pneumoniae* UC41 | 0.06 | 0.5 | 0.06 | 0.06 | 0.25 | 0.13 | 0.06 | 0.06 | 0.13 | 0.13 | 0.06 | 0.06 |
| *S. faecalis* ATCC 7080 | 0.13 | 0.5 | 0.13 | 0.25 | 2 | 0.5 | 0.13 | 0.13 | 0.25 | 0.25 | 1 | 0.13 |
| *Neisseria gonorrhoeae* ISM 68/126 | 0.5 | 16 | 0.5 | 2 | 16 | 8 | 0.25 | 16 | 1 | 4 | 4 | 2 |
| *Haemophilus influenzae* ATCC 19418 | 32 | 32 | 64 | 64 | 64 | 64 | 64 | 64 | 64 | 32 | >128 | 16 |
| *Escherichia coli* SKF 12140 | >128 | 128 | >128 | >128 | >128 | >128 | >128 | >128 | >128 | >128 | >128 | >128 |

The tested compounds showed in vitro antibacterial activity comparable or below that of A 40926.

The two demannosyl derivatives (compounds VIII and X) had better in vitro activity against coagulase-negative staphylococci than the parent compounds (X vs I and VIII vs VII).

Surprisingly, some ester derivatives showed improved in vivo results compared with A 40926 against streptococcal septicsmid in the mouse.

In these in vivo tests control and treatment groups contained five CD-1 mice (Charles River) weighting 18–22 g. They were infected intraperitoneally with 0.5 ml of bacterial suspension prepared by diluting an overnight culture of *Streptococcus pyogenes* $C_{203}$ with sterile peptonized saline. Inocula were adjusted so that untreated animals died of septicsmid within 48 hours. Antibiotics were administered subcutaneously immediately after infection. On the 7th day, the $ED_{50}$ in mg/kg was calculated by the method of Spearman and Kaerber (D. J. Finney, "Statistical Methods in Biological Assay" Griffin page 524, 1952) from the percentages of surviving animals at each dose. The results of the in vivo testing of representative compounds of the invention are summmarized in Table II below:

TABLE II

Activity of A 40926 derivatives in mouse septicemia (*Streptococcus pyogenes* C203)

| Compound | $ED_{50}$ (mg/kg) |
|---|---|
| A 40926 complex | 0.41 |
| A 40926 aglycone | 6.2 |
| A 40926 complex $6^B$-methyl ester (I) | 0.18 |
| A 40926 complex $6^B$-ethyl ester (II) | 0.23 |
| A 40926 complex $6^B$-(2-hydroxyethyl) ester (V) | 0.18 |
| Demannosyl A 40926 complex $6^B$-methyl ester (X) | 0.31 |
| Demannosyl A 40926 complex $6^B$-(2-bromoethyl) ester (VIII) | 0.31 |

In view of the above reported in vivo better antimicrobial activity the compounds of the present invention can effectively be employed as the active ingredients of antimicrobial preparations used in human and veterinary medicine for the prevention and treatment of infectious diseases caused by pathogenic bacteria which are susceptible to said active ingredients.

In general, for antibacterial treatment, A 40926 ester derivatives and A 40926 N-acylaminoglycuronyl aglycone ester derivatives as well as the non-toxic pharmaceutically acceptable salts thereof, can be administered by different routes such as topically or parenterally. The parenteral administration is, in general, the preferred route of administration.

Compositions for injection may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water, is added thereto.

Depending on the route of administration, these compounds can be formulated into various dosage forms.

In some instances, it may be possible to formulate the compounds of the invention in enteric-coated dosage forms for oral administration which may be prepared as known in the art (see for instance "Remington's Pharmaceutical Sciences", fifteenth edition, Mack Publishing Company, Easton, Pa., USA, page 1614).

This could be especially the case when the absorption of the antimicrobial substance in the enteric tract is particularly desired while passing unaltered through the gastric tract.

The amount of active principle to be administered depends on various factors such as the size and condition of the subject to be treated, the route and frequency of administration, and the causative agent involved.

The antibiotic substances of the present invention, namely antibiotic A 40926 complex $6^B$-methyl ester and the physiologically acceptable salts thereof, are generally effective at a daily dosage of between about 0.5 and 50 mg of active ingredient per kilogram of patient body weight, optionally divided into 1 to 4 administrations per day.

Particularly desirable compositions are those prepared in dosage units containing from about 100 to about 5,000 mg per unit.

Sustained-action formulations can be prepared based on different mechanisms and methods, as known in the art.

A preferred method for preparing a sustained-action formulation containing antibiotic A 40926 $6^B$-methyl ester involves the use of a water insoluble form of this antibiotic suspended in an aqueous or oily medium.

These forms, i.e. either as an insoluble salt or as the free acid, in fact, are released very slowly upon intramuscolar injection, because of their low water solubility, thus giving sustained blood levels of the antibiotic substance.

Preparation of Pharmaceutical Compositions

A unit dosage for intramuscolar injection is prepared with 5 ml of sterile suspension USP containing 8% propylene glycol and 500 mg of a physiologically acceptable base addition salt of antibiotic A 40926 $6^B$-monomethyl ester.

A unit dosage form for intramuscolar injection is prepared with 1,000 mg of antibiotic A 40926 $6^B$-monomethyl ester in the water-insoluble acid form suspended in 5 ml of sterile water for injection.

EXAMPLES

Example 1: Preparation of antibiotic A 40926 Complex $6^B$-monomethyl Ester (Compound I)

Antibiotic A 40926 complex (150 mg; 0.0866 mmole), obtained according to EP-A-177882, was dissolved in absolute methanol (30 ml) and the pH adjusted to 2 with concentrated sulfuric acid. The mixture was stirred at room temperature for 26 hours. A precipitate appeared when the pH was brought to 6 with 0.15 ml of triethylamine. After addition of diethyl ether the precipitate was collected, washed thoroughly with diethyl ether and dried. Yield: 150 mg (99%).

Example 2: Preparation of Antibiotic A 40926 Complex $6^B$-monoethyl ester (compound II)

To a stirred solution of antibiotic A 40926 complex (250 mg; 0.144 mmole) in absolute ethanol (30 ml) 2 drops of concentrated sulfuric acid were added at room temperature bringing the pH to 3.23 Hours later the pH was brought to 7 with triethylamine. Upon adding diethyl ether a precipitate appeared which was collected by filtration. This precipitate was suspended in water (130 ml) and the aqueous phase extracted twice with butanol. The extracts were combined and evaporated to a small volume. Upon addition of diethyl ether a solid precipitate was collected yielding 125 mg (yield: 49.2%).

Example 3: Preparation of Antibiotic A 40926 Complex $6^B$-monopropyl ester (compound III)

Antibiotic A 40926 complex (200 mg; 0.115 mole) was dissolved in absolute n-propanol (50 ml). The pH was adjusted to 3 with 40 µl of concentrated sulfuric acid and the solution stirred at room temperature for 15 hours. The pH was adjusted to 7 with $NH_4OH$ and the product precipitated by adding diethyl ether. Yield: 267 mg (91.2%)

Example 4: Preparation of Antibiotic A 40926 Complex $6^B$-monobutyl ester (compound IV)

Antibiotic A 40926 complex (200 mg; 0.115 mmole) was dissolved in absolute butanol (100 ml), the pH adjusted as above and the solution left stand for 3 days at room temperature. The pH was then raised to 5 with 40 µl of $NH_4OH$ (32%), 100 ml of water were added, the organic layer was separated and the aqueous phase was extracted twice with butanol. The butanol extracts were pooled together and reduced to a small volume. Upon addition of diethyl ether, 136 mg (yield: 65.9%) of the title compound were collected.

Example 5: Preparation of Antibiotic A 40926 Complex $6^B$-(2-hydroxyethyl) ester (Compound V)

Antibiotic A 40926 complex (150 mg; 0.0866 mmole) was dissolved in ethylene glycol (20 ml) with stirring at room temperature. The pH was adjusted to 2 with 40 µl of concentrated sulfuric acid and the mixture left stand for 3 days. The solution was reduced to about 5 ml and directly used for a separation with preparative HPLC with 5 l of a 31% $CH_3CN$ in 0.02M $NaH_2PO_4$ (isocratic). The usual isolation procedure yielded 27 mg of very pure ester (yield: 18%).

Example 6: Preparation of Antibiotic A 40926 Complex $6^B$-(4-hydroxybutyl) ester (compound VI)

To a solution of antibiotic A 40926 complex (400 mg; 0.230 mmole) in 25 ml of 1,4-butanediol were added 60 µl of concentrated sulfuric acid with stirring at room temperature and the solution was left stand for 55 hours. The solution was diluted with 50 ml of butanol and upon addition of diethyl ether a solid precipitated which was collected and purified with preparative HPLC using 5 l of 32% $CH_3CN$ in 0.02M $NaH_2PO_4$. Using the usual isolation procedure 227 mg (54.5%) of the title compound were obtained.

Example 7: Preparation of Antibiotic A 40926 Complex $6^B$-(2-bromoethyl) ester (Compound VII) and its Demannosylated Analogue (Compound VIII)

Antibiotic A 40926 complex (300 mg; 0.173 mmole) was dissolved in 5 ml of 2-bromoethanol and the solution stirred for 22 hours at 0° C. The temperature was raised to room temperature and stirring continued for 15 hours. The starting material was completely transformed into two more lipophilic compounds accompanied by large amounts of aglycone and mannosyl aglycone. The solution was cooled to 0° C. Upon adding diethyl ether a precipitate appeared which was collected (295 mg) and then separated using preparative HPLC (RP-18, 10 µm), with 34% acetonitrile in 0.02M $NaH_2PO_4$ buffer. Two fractions of 15 mg (yield: 4.7%) and 27 mg (yield: 9.3%) were isolated which corresponded to A 40926 $6^B$-(2-bromoethyl) ester (VII) and its demannosylated derivative (VIII), respectively.

Example 8: Preparation of $N^{15}$-benzyl A 40926 Complex (Compound IX)

The antibiotic A 40926 complex (1.5 g; 0.87 mmole) was dissolved in 100 ml of dry DMF and the solution cooled to 0° C. The pH was adjusted to 7 with 0.26 ml (1.83 mmole) of triethylamine. Benzyl bromide (0.11 ml; 0.96 mmole) was added under stirring and 7 hours later once more 20.6.µl (0.145 mmole) of this reactant were added. After 48 hours diethyl ether was added, the precipitate collected, washed carefully with diethyl ether and dried. Yield: 1.53 g (96.7%).

Example 9: Preparation of $O^{42}$-demannosyl A 40926 $6^B$-methyl ester (i.e. A 40926 N-acylaminoglucuronyl aglycone $6^B$-methylester) (Compound X)

To a solution of 650 mg (0.086 mmole) of the antibiotic A 40926 complex $6^B$-methyl ester (I) in 7 ml of DMSO 50 µl of 37% HCl were added, bringing the pH to 2. The mixture was heated at 50° C. for 24 hours. Then additional 25 µl of HCl were added and after 48 hours further 15 µl thus maintaining the pH at 2.7 Days later HPLC showed the disappearance of the antibiotic A 40926 complex and the appearance of $O^{42}$-demannosyl A 40926 complex $6^B$-methyl ester and the corresponding aglycone in a ratio 1.4:1.0. The reaction mixture was poured into a mixture of 15 ml of diethyl ether and 5 ml of butanol, yielding a solid precipitate (653 mg) which was collected by filtration and separated with preparative HPLC using isocratic conditions with 30% $CH_3CN$/70% 0.02M $NaH_2PO_4$ (5 l), then 33% $CH_3CN$/67% 0.02M $NaH_2PO_4$ (2 l), and finally 40% $CH_3CN$/60% 0.02M $NaH_2PO_4$ (2 l). The fractions containing the desired compound were pooled, reduced to a smaller volume and extracted three times with butanol; the butanolic phase was reduced to a small volume. Upon addition of diethyl ether 68 mg (yield: 11.5%) of the title compound were collected.

General Experimental Conditions and Analytical Procedures

Evaporation of solvents was carried out after addition of n-butanol to prevent foaming, with a rotary evaporator at 45° C. under vacuum. If not otherwise stated the final products were washed with diethyl ether and dried at 40° C. under vacuum. Separations were performed using silanized Silica gel 60 (0.06–0.2 mm) or Silica gel RP-8 (LiChroprep 40–63 μm; Merck) with normal columns or with preparative HPLC using a Waters model 590 equipped with a 481 UV-detector and a preparative column LiChrosorb RP-18, 10 μm (size 250=50 mm, loop 5 ml, flow rate 30 ml/min). HPLC was also used to monitor reactions, chromatographic fractions and purity of the compounds using a Varian 5000 machine equipped with a 2050 UV-detector at 254 nm and and columns LiChrosorb RP-8, 5 μm or RP-18, 10 μm (125×4 and 250×4 mm, respectively). Injection volume: 10 μ; flow rate: 1.5 ml/min.; mobile phase, (A) 0.02M aq. $NaH_2PO_4$, (B) $CH_3CN$.

All compounds were analyzed for C, H and N after drying at 140° C. under $N_2$. weight loss was determined by thermogravimetric analysis (TGA) at 140° C.; inorganic residue was determined after heating the samples at 900° C. in $O_2$. Cl and Br, when present, were determined on samples dried as described above. The analytical results were in accordance with the theoretical values.

The $^1$H-NMR spectra were obtained with AM 250 or AM 500 Bruker instruments equipped with an Aspect 3000 computer. The spectra were recorded at 40° C. in DMSO-$d_6$ solution with TMS as internal standard.

FAB-MS positive ion spectra were obtained on a Kratos MS-50 focusing mass spectrometer of 3000 dalton mass range, using 8 kV accelerating voltage. The instrument was operating under computer control. To obtain high quality data, a DS-90 data system in "raw data" acquisition was used. For mass calibration a mixture of CsI and NaI was used. For FAB, a saddle field atom gun was used with Xe gas ($2\times10^{-5}$ torr pressure) at 6 kV voltage and 1 mA current. The samples were dissolved in methanol or DMF depending on solubility. 1 μl of this solution was mixed with 1 μl of thioglycerol matrix containing 0.1 μl $CH_3COOH$ on the target.

Table III summarizes some physico-chemical characteristics of representative compounds of the invention (the compounds of formula I wherein R' represents ($C_{10}$–$C_{11}$) alkyl and $R_2$, $R_3$, and M are as indicated):

TABLE III

A 40926 derivatives

| Compound | $R_2$ | $R_3$ | M | Yield (%) | Formula | MH (calc.) | MH (FAB, found) |
|---|---|---|---|---|---|---|---|
| I | H | $CH_3$ | α-D-mannosyl | 99 | $C_{84}H_{90}Cl_2N_8O_{29}$ | 1745.6 | 1745.5 |
| II | H | $C_2H_5$ | " | 49 | $C_{85}H_{92}Cl_2N_8O_{29}$ | 1759.5 | 1759.6 |
| III | H | $C_3H_7(n)$ | " | 91 | $C_{86}H_{94}Cl_2N_8O_{29}$ | 1773.6 | 1773.4 |
| IV | H | $C_4H_9(n)$ | " | 66 | $C_{87}H_{96}Cl_2N_8O_{29}$ | 1787.6 | 1787.6 |
| V | H | $C_2H_4OH$ | " | 18[a] | $C_{85}H_{92}Cl_2N_8O_{30}$ | 1775.5 | 1775.4 |
| VI | H | $C_4H_8OH$ | " | 55[a] | $C_{87}H_{96}Cl_2N_8O_{30}$ | 1825.5 | 1825.4 |
| VII | H | $C_2H_4Br$ | " | 5[a] | $C_{85}H_{91}BrCl_2N_8O_{29}$ | 1837.5 | 1859.4[b] |
| VIII | H | $C_2H_4Br$ | H | 9[a] | $C_{79}H_{81}BrCl_2N_8O_{24}$ | 1675.4 | 1697.4[b] |
| IX | $PhCH_2$ | H | α-D-mannosyl | 97 | $C_{90}H_{94}Cl_2N_8O_{29}$ | 1821.6 | 1821.8 |
| X | H | $CH_3$ | H | 12[a] | $C_{78}H_{80}Cl_2N_8O_{24}$ | 1583.5 | 1583.5 |

Note:
[a] after prep. HPLC
[b] $M^+ + Na$
[c] mass of $MH^+$ based on isotope average

We claim:

1. An antibiotic A 40926 ester derivative of formula I

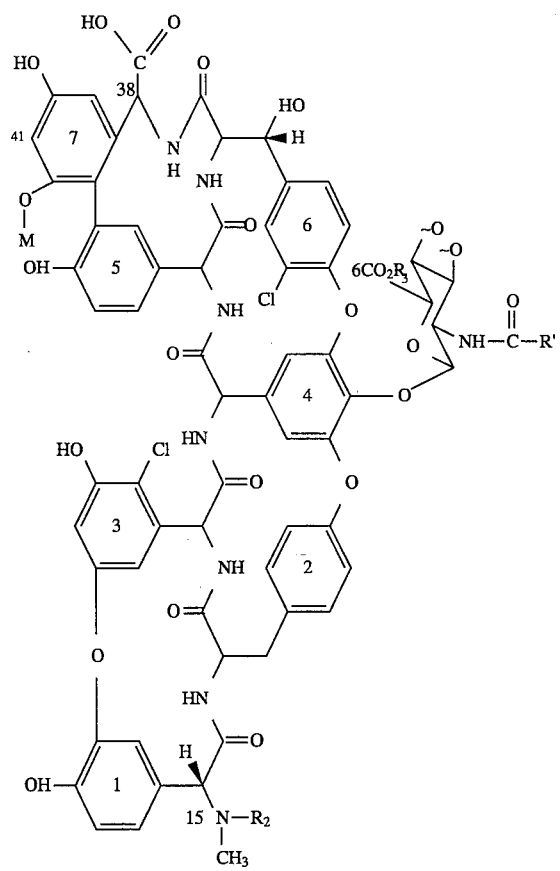

wherein

R₂ represents hydrogen or a protecting group of the amine function;

M represents hydrogen, α-D-mannopyranosyl or 6-O-acetyl-α-D-mannopyranosyl;

R' represents $(C_{10}-C_{11})$ alkyl;

$R_3$ is represented by $(C_1-C_6)$ alkyl, hydroxy $(C_1-C_6)$ alkyl, or halo $(C_1-C_6)$ alkyl;

and the addition salts thereof.

2. The compound according to claim 1 wherein $R_2$ represents hydrogen, and $R_3$ is represented by $C_1-C_4$) alkyl, hydroxy $(C_1-C_4)$ alkyl, or halo $(C_1-C_4)$ alkyl.

3. The compound according to claim 1 where $R_2$ represents hydrogen, M is 6-O-acetyl-α-D-mannopyranosyl or α-D-mannopyranosyl, and $R_3$ is represented by $(C_1-C_4)$ alkyl, hydroxy $(C_1-C_4)$ alkyl, or halo $(C_1-C_4)$ alkyl.

4. The compound according to claim 1 wherein $R_2$ represents hydrogen, M is 6-O-acetyl-α-D-mannopyranosyl or α-D-mannopyranosyl, and $R_3$ is $(C_1-C_4)$ alkyl or 2-hydroxyethyl.

5. The compound according to claim 1 wherein $R_2$ represents hydrogen, M is α-D-mannopyranosyl, and $R_3$ is methyl or 2-hydroxyethyl.

6. The compound according to claim 1 wherein $R_2$ represents hydrogen, M is α-D-mannopyranosyl, R' is selected from n-decyl and 9-methyldecyl, and $R_3$ is methyl or 2-hydroxyethyl.

7. A pharmaceutical composition comprising a compound of claim 1 in admixture with a pharmaceutically acceptable carrier.

8. A method for the treatment of bacterial infections caused by either gram positive bacteria or by *Neisseria gonorrhoeae* comprising administering an anti-bacterially effective amount of a compound according to claim 1 to a patient in need thereof.

* * * * *